United States Patent
Arcand

(10) Patent No.: US 8,647,376 B2
(45) Date of Patent: Feb. 11, 2014

(54) BALLOON FOLD DESIGN FOR DEPLOYMENT OF BIFURCATED STENT PETAL ARCHITECTURE

(75) Inventor: Benjamin Arcand, Minneapolis, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 457 days.

(21) Appl. No.: 11/693,957

(22) Filed: Mar. 30, 2007

(65) Prior Publication Data

US 2008/0243221 A1   Oct. 2, 2008

(51) Int. Cl.
  *A61F 2/06* (2013.01)
(52) U.S. Cl.
  USPC .......................................... 623/1.11
(58) Field of Classification Search
  USPC ............. 604/103.06, 103.07, 103.08, 103.14, 604/509; 606/192, 194; 623/1.11, 1.12; 493/405; 428/9, 34.1–36.92, 12; 446/487, 488; 264/507
  See application file for complete search history.

(56) References Cited

U.S. PATENT DOCUMENTS

| | | | | |
|---|---|---|---|---|
| 3,643,268 A | * | 2/1972 | Stamberger ..................... | 428/12 |
| 4,309,994 A | | 1/1982 | Grunwald ................. | 128/214 R |
| 4,769,005 A | | 9/1988 | Ginsburg et al. ............... | 604/53 |
| 4,774,949 A | | 10/1988 | Fogarty ....................... | 128/348.1 |
| 4,896,670 A | | 1/1990 | Crittenden ................... | 606/194 |
| 4,905,667 A | | 3/1990 | Foerster et al. .................. | 128/4 |
| 4,906,244 A | | 3/1990 | Pinchuk et al. ............... | 606/194 |
| 4,935,190 A | | 6/1990 | Tennerstedt .................. | 264/529 |
| 4,994,071 A | | 2/1991 | MacGregor .................. | 606/194 |
| 5,037,392 A | | 8/1991 | Hillstead ......................... | 604/96 |
| 5,053,007 A | | 10/1991 | Euteneuer ....................... | 604/96 |
| 5,087,246 A | | 2/1992 | Smith ............................. | 604/96 |
| 5,147,302 A | | 9/1992 | Euteneuer et al. ............ | 604/103 |
| 5,163,989 A | | 11/1992 | Campbell et al. .............. | 65/110 |
| 5,209,799 A | | 5/1993 | Vigil ............................. | 156/156 |
| 5,226,887 A | | 7/1993 | Farr et al. ........................ | 604/96 |
| 5,234,727 A | * | 8/1993 | Hoberman ...................... | 428/12 |
| 5,306,246 A | | 4/1994 | Sahatjian et al. .............. | 604/96 |
| 5,318,587 A | | 6/1994 | Davey ........................... | 606/194 |

(Continued)

FOREIGN PATENT DOCUMENTS

| | | |
|---|---|---|
| CA | 2220864 | 7/1999 |
| DE | 9014845 | 2/1991 |

(Continued)

OTHER PUBLICATIONS

Chevalier, M.D., Bernard, "Placement of Coronary Stents in Bifurcation Lesions by the "Culotte" Technique," *The American Journal of Cardiology*, vol. 82, pp. 943-949 (Oct. 15, 1998).

(Continued)

*Primary Examiner* — Thomas McEvoy
(74) *Attorney, Agent, or Firm* — Vidas, Arrett & Steinkraus, P.A.

(57) ABSTRACT

A balloon fold design for efficient expansion of a side branch assembly in a bifurcated stent. The design involves forming a cup arrangement by folding the radial end of the side branch balloon structure into the luminal end of the side branch balloon structure and then folding the cup down into an orderly discus arrangement. The folding pattern allows for the side branch balloon structure to inflate in a sweeping rotational manner efficiently pushing the side branch assembly petals out and away from the main body of the stent with a low risk of the balloon becoming entangled or damaged by its contact with the petals. The design also allows for the expansion force to be applied at the appropriate time in the optimally needed direction by initially being oriented in a predominantly circumferential direction which is gradually shifting to a predominantly radial direction. In addition, the fold design reduces the overall volume and profile of the side branch balloon structure.

17 Claims, 10 Drawing Sheets

(56) References Cited

U.S. PATENT DOCUMENTS

| | | | |
|---|---|---|---|
| 5,342,307 A | 8/1994 | Euteneuer et al. | 604/103 |
| 5,342,387 A | 8/1994 | Summers | 606/198 |
| 5,350,361 A | 9/1994 | Tsukashima et al. | 604/96 |
| 5,387,235 A | 2/1995 | Chuter | 623/1 |
| 5,456,666 A | 10/1995 | Campbell et al. | 604/96 |
| 5,456,712 A | 10/1995 | Maginot | 623/1 |
| 5,458,572 A | 10/1995 | Campbell et al. | 604/96 |
| 5,476,471 A | 12/1995 | Shifrin et al. | 606/151 |
| 5,478,319 A | 12/1995 | Campbell et al. | 604/96 |
| 5,487,730 A | 1/1996 | Marcadis et al. | 604/96 |
| 5,591,228 A | 1/1997 | Edoga | 623/1 |
| 5,607,444 A | 3/1997 | Lam | 606/194 |
| 5,609,605 A | 3/1997 | Marshall et al. | 606/191 |
| 5,609,627 A | 3/1997 | Goicoechea et al. | 623/1 |
| 5,613,980 A | 3/1997 | Chauhan | 606/194 |
| 5,617,878 A | 4/1997 | Taheri | 128/898 |
| 5,632,762 A | 5/1997 | Myler | 606/194 |
| 5,632,763 A | 5/1997 | Glastra | 606/194 |
| 5,632,772 A | 5/1997 | Alcime et al. | 623/1 |
| 5,636,641 A | 6/1997 | Fariabi | 600/585 |
| 5,669,924 A | 9/1997 | Shaknovich | 606/108 |
| 5,669,932 A | 9/1997 | Fischell et al. | 606/198 |
| 5,676,697 A | 10/1997 | McDonald | 623/1 |
| 5,683,450 A | 11/1997 | Goicoechea et al. | 623/1 |
| 5,697,971 A | 12/1997 | Fischell et al. | 623/1 |
| 5,707,348 A | 1/1998 | Krogh | 602/41 |
| 5,709,713 A | 1/1998 | Evans et al. | 623/1 |
| 5,718,684 A | 2/1998 | Gupta | 604/96 |
| 5,720,735 A | 2/1998 | Dorros | 604/284 |
| 5,746,745 A | 5/1998 | Abele et al. | 606/108 |
| 5,749,825 A | 5/1998 | Fischell et al. | 600/3 |
| 5,749,890 A | 5/1998 | Shaknovich | 606/198 |
| 5,755,734 A | 5/1998 | Richter et al. | 606/194 |
| 5,755,735 A | 5/1998 | Richter et al. | 606/194 |
| 5,755,771 A | 5/1998 | Penn et al. | 623/1 |
| 5,755,773 A | 5/1998 | Evans et al. | 623/1 |
| 5,755,778 A | 5/1998 | Kleshinski | 623/1 |
| 5,782,906 A | 7/1998 | Marshall et al. | 623/1 |
| 5,824,036 A | 10/1998 | Lauterjung | 623/1 |
| 5,824,040 A | 10/1998 | Cox et al. | 623/1 |
| 5,827,320 A | 10/1998 | Richter et al. | 606/194 |
| 5,833,657 A | 11/1998 | Reinhardt et al. | 604/96 |
| 5,851,464 A | 12/1998 | Davila et al. | 264/103 |
| 5,868,777 A | 2/1999 | Lam | 606/194 |
| 5,882,334 A | 3/1999 | Sepetka et al. | 604/96 |
| 5,893,887 A | 4/1999 | Jayaraman | 623/1 |
| 5,899,842 A * | 5/1999 | Di Pilla | 493/405 |
| 5,961,548 A | 10/1999 | Shmulewitz | 623/1 |
| 5,972,017 A | 10/1999 | Berg et al. | 606/198 |
| 6,013,054 A | 1/2000 | Jiun Yan | 604/96 |
| 6,013,055 A | 1/2000 | Bampos et al. | 604/96 |
| 6,017,324 A | 1/2000 | Tu et al. | 604/96 |
| 6,017,363 A | 1/2000 | Hojeibane | 623/1 |
| 6,030,414 A | 2/2000 | Taheri | 623/1 |
| 6,033,380 A | 3/2000 | Butaric et al. | 604/96 |
| 6,033,434 A | 3/2000 | Borghi | 623/1 |
| 6,033,435 A | 3/2000 | Penn et al. | 623/1 |
| 6,056,775 A | 5/2000 | Borghi et al. | 623/1.16 |
| 6,059,824 A | 5/2000 | Taheri | 623/1 |
| 6,068,655 A | 5/2000 | Seguin et al. | 623/1 |
| 6,071,285 A | 6/2000 | Lashinski et al. | 606/108 |
| 6,086,611 A | 7/2000 | Duffy et al. | 623/1 |
| 6,093,203 A | 7/2000 | Uflacker | 612/1.12 |
| 6,096,073 A | 8/2000 | Webster et al. | 623/1.16 |
| 6,099,497 A | 8/2000 | Adams et al. | 604/96.01 |
| 6,113,579 A | 9/2000 | Eidenschink et al. | 604/264 |
| 6,117,117 A | 9/2000 | Mauch | 604/284 |
| 6,117,156 A | 9/2000 | Richter et al. | 606/194 |
| 6,126,652 A | 10/2000 | McLeod et al. | 606/1 |
| 6,129,738 A | 10/2000 | Lashinski et al. | 606/194 |
| 6,135,982 A | 10/2000 | Campbell | 604/96.01 |
| 6,142,973 A | 11/2000 | Carleton et al. | 604/96 |
| 6,143,002 A | 11/2000 | Vietmeier | 606/108 |
| 6,159,238 A | 12/2000 | Killion et al. | 612/1.11 |
| 6,165,195 A | 12/2000 | Wilson et al. | 606/194 |
| 6,168,621 B1 | 1/2001 | Vrba | 623/1.2 |
| 6,183,509 B1 | 2/2001 | Dibie | 623/1.35 |
| 6,203,568 B1 | 3/2001 | Lombardi et al. | 623/1.13 |
| 6,210,380 B1 | 4/2001 | Mauch | 604/284 |
| 6,210,429 B1 | 4/2001 | Vardi et al. | 623/1.11 |
| 6,210,433 B1 | 4/2001 | Larre | 623/1.15 |
| 6,254,593 B1 | 7/2001 | Wilson | 606/1.11 |
| 6,258,115 B1 | 7/2001 | Dubrul | 606/200 |
| 6,258,116 B1 | 7/2001 | Hojeibane | 623/1.16 |
| 6,261,305 B1 | 7/2001 | Marotta et al. | 606/200 |
| 6,261,316 B1 | 7/2001 | Shaolian et al. | 623/1.11 |
| 6,264,662 B1 | 7/2001 | Lauterjung | 606/108 |
| 6,264,686 B1 | 7/2001 | Rieu et al. | 623/1.16 |
| 6,286,866 B1 * | 9/2001 | Satge et al. | 280/743.1 |
| 6,290,673 B1 | 9/2001 | Shanley | 604/102.02 |
| 6,293,968 B1 | 9/2001 | Taheri | 623/1.15 |
| 6,325,826 B1 | 12/2001 | Vardi et al. | 623/1.35 |
| 6,334,864 B1 | 1/2002 | Amplatz et al. | 606/200 |
| 6,346,089 B1 | 2/2002 | Dibie | 603/1.15 |
| 6,355,060 B1 | 3/2002 | Lenker et al. | 623/1.34 |
| 6,361,544 B1 | 3/2002 | Wilson et al. | 606/194 |
| 6,361,555 B1 | 3/2002 | Wilson | 623/1.11 |
| 6,383,213 B2 | 5/2002 | Wilson et al. | 623/1.11 |
| 6,395,018 B1 | 5/2002 | Castaneda | 623/1.13 |
| 6,436,104 B2 | 8/2002 | Hojeibane | 606/108 |
| 6,436,134 B2 | 8/2002 | Richter et al. | 623/1.15 |
| 6,508,836 B2 | 1/2003 | Wilson et al. | 623/1.35 |
| 6,517,558 B2 | 2/2003 | Gittings et al. | 606/153 |
| 6,520,988 B1 | 2/2003 | Colombo et al. | 623/1.35 |
| 6,540,779 B2 | 4/2003 | Richter et al. | 623/1.35 |
| 6,547,709 B1 * | 4/2003 | Dennis | 493/405 |
| 6,579,309 B1 | 6/2003 | Loos et al. | 623/1.16 |
| 6,579,312 B2 | 6/2003 | Wilson et al. | 623/1.35 |
| 6,582,394 B1 | 6/2003 | Reiss et al. | 604/96.01 |
| 6,596,020 B2 | 7/2003 | Vardi et al. | 623/1.11 |
| 6,599,316 B2 | 7/2003 | Vardi et al. | 623/1.15 |
| 6,645,242 B1 | 11/2003 | Quinn | 623/1.16 |
| 6,689,156 B1 | 2/2004 | Davidson et al. | 623/1.11 |
| 6,692,483 B2 | 2/2004 | Vardi et al. | 604/529 |
| 6,695,877 B2 | 2/2004 | Brucker et al. | 623/1.16 |
| 6,706,062 B2 | 3/2004 | Vardi et al. | 623/1.15 |
| 6,749,628 B1 | 6/2004 | Callol et al. | 623/1.15 |
| 6,776,793 B2 | 8/2004 | Brown et al. | 623/1.15 |
| 6,811,566 B1 | 11/2004 | Penn et al. | 623/1.15 |
| 6,835,203 B1 | 12/2004 | Vardi et al. | 623/1.34 |
| 6,858,038 B2 | 2/2005 | Heuser | 623/1.35 |
| 6,884,258 B2 | 4/2005 | Vardi et al. | 623/1.11 |
| 6,896,699 B2 | 5/2005 | Wilson et al. | 623/1.35 |
| 6,932,837 B2 | 8/2005 | Amplatz et al. | 623/1.15 |
| 6,946,092 B1 | 9/2005 | Berolino et al. | 264/512 |
| 6,955,687 B2 | 10/2005 | Richter et al. | 623/1.35 |
| 6,955,688 B2 | 10/2005 | Wilson et al. | 623/1.35 |
| 6,962,602 B2 | 11/2005 | Vardi et al. | 623/1.11 |
| 7,018,400 B2 | 3/2006 | Lashinski et al. | 623/1.11 |
| 7,056,323 B2 | 6/2006 | Mareiro et al. | 606/108 |
| 7,060,091 B2 | 6/2006 | Killion et al. | 623/1.15 |
| 2001/0003161 A1 | 6/2001 | Vardi et al. | 623/1.11 |
| 2001/0004706 A1 | 6/2001 | Hojeibane | 623/1.11 |
| 2001/0004707 A1 | 6/2001 | Dereume et al. | 623/1.16 |
| 2001/0012927 A1 | 8/2001 | Mauch | 604/284 |
| 2001/0016766 A1 | 8/2001 | Vardi et al. | 623/1.11 |
| 2001/0016767 A1 | 8/2001 | Wilson et al. | 623/1.11 |
| 2001/0016768 A1 | 8/2001 | Wilson et al. | 623/1.11 |
| 2001/0025195 A1 | 9/2001 | Shaolian et al. | 623/1.13 |
| 2001/0027291 A1 | 10/2001 | Shanley | 604/104 |
| 2001/0027338 A1 | 10/2001 | Greenberg | 623/1.13 |
| 2001/0029396 A1 | 10/2001 | Wilson et al. | 623/1.11 |
| 2001/0037116 A1 | 11/2001 | Wilson et al. | 606/108 |
| 2001/0037138 A1 | 11/2001 | Wilson et al. | 623/1.11 |
| 2001/0039448 A1 | 11/2001 | Dibie | 623/1.16 |
| 2001/0049552 A1 | 12/2001 | Richter et al. | 623/1.15 |
| 2001/0056297 A1 | 12/2001 | Hojeibane | 623/1.16 |
| 2002/0013618 A1 | 1/2002 | Marotta et al. | 623/1.15 |
| 2002/0013619 A1 | 1/2002 | Shanley | 623/1.15 |
| 2002/0022874 A1 | 2/2002 | Wilson | 623/1.11 |
| 2002/0026232 A1 | 2/2002 | Marotta et al. | 623/1.16 |
| 2002/0035392 A1 | 3/2002 | Wilson | 623/1.11 |
| 2002/0042650 A1 | 4/2002 | Vardi et al. | 623/1.35 |
| 2002/0052648 A1 | 5/2002 | McGuckin, Jr. et al. | 623/1.35 |

(56) References Cited

U.S. PATENT DOCUMENTS

| | | | |
|---|---|---|---|
| 2002/0072790 A1 | 6/2002 | McGuckin, Jr. et al. | 623/1.12 |
| 2002/0111675 A1 | 8/2002 | Wilson | 623/1.35 |
| 2002/0156516 A1 | 10/2002 | Vardi et al. | 623/1.11 |
| 2002/0156517 A1 | 10/2002 | Perouse | 623/1.11 |
| 2002/0165604 A1 | 11/2002 | Shanley | 623/1.15 |
| 2002/0173835 A1 | 11/2002 | Bourang et al. | 623/1.11 |
| 2002/0173840 A1 | 11/2002 | Brucker et al. | 623/1.16 |
| 2002/0183763 A1 | 12/2002 | Callol et al. | 606/108 |
| 2002/0193872 A1 | 12/2002 | Trout, III et al. | 623/1.34 |
| 2002/0193873 A1 | 12/2002 | Brucker et al. | 623/1.35 |
| 2003/0009209 A1 | 1/2003 | Hojeibane | 623/1.11 |
| 2003/0028233 A1 | 2/2003 | Vardi et al. | 623/1.11 |
| 2003/0050688 A1 | 3/2003 | Fischell et al. | 623/1.11 |
| 2003/0055378 A1 | 3/2003 | Wang et al. | 604/103.07 |
| 2003/0055483 A1 | 3/2003 | Gumm | 623/1.11 |
| 2003/0074047 A1 | 4/2003 | Richter | 623/1.11 |
| 2003/0093109 A1 | 5/2003 | Mauch | 606/194 |
| 2003/0097169 A1 | 5/2003 | Brucker | 623/1.11 |
| 2003/0114912 A1 | 6/2003 | Sequin et al. | 623/1.11 |
| 2003/0125791 A1 | 7/2003 | Sequin et al. | 623/1.11 |
| 2003/0125802 A1 | 7/2003 | Callol et al. | 623/1.35 |
| 2003/0135259 A1 | 7/2003 | Simso | 623/1.12 |
| 2003/0163082 A1 | 8/2003 | Mertens | 604/43 |
| 2003/0181923 A1 | 9/2003 | Vardi | 606/108 |
| 2003/0195606 A1 | 10/2003 | Davidson et al. | 623/1.11 |
| 2004/0006381 A1 | 1/2004 | Sequin et al. | 623/1.12 |
| 2004/0015227 A1 | 1/2004 | Vardi et al. | 623/1.16 |
| 2004/0044396 A1 | 3/2004 | Clerc et al. | 623/1.13 |
| 2004/0059406 A1 | 3/2004 | Cully et al. | 623/1.11 |
| 2004/0088007 A1 | 5/2004 | Eidenschink | 607/1 |
| 2004/0117003 A1 | 6/2004 | Ouriel et al. | 623/1.35 |
| 2004/0133268 A1 | 7/2004 | Davidson et al. | 623/1.35 |
| 2004/0138732 A1 | 7/2004 | Suhr et al. | 623/1.11 |
| 2004/0138737 A1 | 7/2004 | Davidson et al. | 623/1.35 |
| 2004/0148006 A1 | 7/2004 | Davidson et al. | 623/1.11 |
| 2004/0172121 A1 | 9/2004 | Eidenschink et al. | 623/1.11 |
| 2004/0186560 A1 | 9/2004 | Alt | 623/1.35 |
| 2004/0225345 A1 | 11/2004 | Fischell et al. | 623/1.11 |
| 2004/0267352 A1 | 12/2004 | Davidson et al. | 623/1.15 |
| 2005/0004656 A1 | 1/2005 | Das | 623/1.16 |
| 2005/0010278 A1 | 1/2005 | Vardi et al. | 623/1.35 |
| 2005/0015108 A1 | 1/2005 | Williams et al. | 606/194 |
| 2005/0015135 A1 | 1/2005 | Shanley | 623/1.11 |
| 2005/0060027 A1 | 3/2005 | Khenansho et al. | 623/1.35 |
| 2005/0096726 A1 | 5/2005 | Sequin et al. | 623/1.12 |
| 2005/0102019 A1 | 5/2005 | Yadin | 623/1.11 |
| 2005/0102021 A1 | 5/2005 | Osborne | 623/1.13 |
| 2005/0102023 A1 | 5/2005 | Yadin et al. | 623/1.15 |
| 2005/0119731 A1 | 6/2005 | Brucker et al. | 623/1.35 |
| 2005/0125076 A1 | 6/2005 | Ginn | 623/23.65 |
| 2005/0131526 A1 | 6/2005 | Wong | 623/1.15 |
| 2005/0149161 A1 | 7/2005 | Eidenschink et al. | 623/1.11 |
| 2005/0154442 A1 | 7/2005 | Eidenschink et al. | 623/1.11 |
| 2005/0154444 A1 | 7/2005 | Quadri | 623/1.13 |
| 2005/0183259 A1 | 8/2005 | Eidenschink et al. | 29/508 |
| 2005/0209673 A1 | 9/2005 | Shaked | 623/1.11 |
| 2005/0228483 A1 | 10/2005 | Kaplan et al. | 623/1.15 |
| 2006/0036315 A1 | 2/2006 | Yadin et al. | 623/1.35 |
| 2006/0041303 A1 | 2/2006 | Israel | 623/1.11 |
| 2006/0079956 A1 | 4/2006 | Eigler et al. | 623/1.35 |
| 2006/0173528 A1 | 8/2006 | Feld et al. | 623/1.15 |
| 2007/0073376 A1 | 3/2007 | Krolik et al. | 623/1.11 |

FOREIGN PATENT DOCUMENTS

| | | |
|---|---|---|
| DE | 29701758 | 3/1997 |
| DE | 29701883 | 5/1997 |
| EP | 0479730 | 10/1991 |
| EP | 0751752 | 1/1997 |
| EP | 0783873 | 7/1997 |
| EP | 0804907 | 11/1997 |
| EP | 0479557 | 7/1998 |
| EP | 0876805 | 11/1998 |
| EP | 0880949 | 12/1998 |
| EP | 0891751 | 1/1999 |
| EP | 0895759 | 2/1999 |
| EP | 0904745 | 3/1999 |
| EP | 0937442 | 8/1999 |
| EP | 0347023 | 12/1999 |
| EP | 1031328 | 8/2000 |
| EP | 1031329 | 8/2000 |
| EP | 0883384 | 12/2000 |
| EP | 0862392 | 8/2001 |
| EP | 0808140 | 12/2001 |
| EP | 0884028 | 2/2002 |
| EP | 1190685 | 3/2002 |
| EP | 0897700 | 7/2002 |
| EP | 0684022 | 2/2004 |
| EP | 1157674 | 7/2005 |
| EP | 1031330 | 11/2005 |
| EP | 1070513 | 6/2006 |
| FR | 2678508 | 1/1993 |
| FR | 2740346 | 10/1995 |
| FR | 2756173 | 11/1996 |
| GB | 2337002 | 5/1998 |
| WO | 88/06026 | 8/1988 |
| WO | 95/21592 | 8/1995 |
| WO | 96/29955 | 10/1996 |
| WO | 96/34580 | 11/1996 |
| WO | 96/41592 | 12/1996 |
| WO | 97/07752 | 3/1997 |
| WO | 97/15346 | 5/1997 |
| WO | 97/16217 | 5/1997 |
| WO | 97/26936 | 7/1997 |
| WO | 97/41803 | 11/1997 |
| WO | 97/45073 | 12/1997 |
| WO | 97/46174 | 12/1997 |
| WO | 98/19628 | 5/1998 |
| WO | 98/36709 | 8/1998 |
| WO | 98/37833 | 9/1998 |
| WO | 98/47447 | 10/1998 |
| WO | 98/48879 | 11/1998 |
| WO | 99/03426 | 1/1999 |
| WO | 99/04726 | 2/1999 |
| WO | 99/15103 | 4/1999 |
| WO | 99/15109 | 4/1999 |
| WO | 99/24104 | 5/1999 |
| WO | 99/34749 | 7/1999 |
| WO | 99/36002 | 7/1999 |
| WO | 99/36015 | 7/1999 |
| WO | 99/44539 | 9/1999 |
| WO | 99/56661 | 11/1999 |
| WO | 99/65419 | 12/1999 |
| WO | 00/07523 | 2/2000 |
| WO | 00/10489 | 3/2000 |
| WO | 00/16719 | 3/2000 |
| WO | 00/27307 | 5/2000 |
| WO | 00/27463 | 5/2000 |
| WO | 00/28922 | 5/2000 |
| WO | 01/45594 | 6/2000 |
| WO | 00/44307 | 8/2000 |
| WO | 00/44309 | 8/2000 |
| WO | 00/47134 | 8/2000 |
| WO | 00/48531 | 8/2000 |
| WO | 00/49951 | 8/2000 |
| WO | 00/51523 | 9/2000 |
| WO | 00/57813 | 10/2000 |
| WO | 00/67673 | 11/2000 |
| WO | 00/71054 | 11/2000 |
| WO | 00/71055 | 11/2000 |
| WO | 00/74595 | 12/2000 |
| WO | 01/21095 | 3/2001 |
| WO | 01/21109 | 3/2001 |
| WO | 01/21244 | 3/2001 |
| WO | 01/35715 | 5/2001 |
| WO | 01/35863 | 5/2001 |
| WO | 01/39697 | 6/2001 |
| WO | 01/39699 | 6/2001 |
| WO | 01/41677 | 6/2001 |
| WO | 01/43665 | 6/2001 |
| WO | 01/43809 | 6/2001 |
| WO | 01/45785 | 6/2001 |
| WO | 01/49342 | 7/2001 |

(56) References Cited

FOREIGN PATENT DOCUMENTS

| WO | 01/54621 | 8/2001 |
|---|---|---|
| WO | 01/54622 | 8/2001 |
| WO | 01/58385 | 8/2001 |
| WO | 01/60284 | 8/2001 |
| WO | 01/70294 | 9/2001 |
| WO | 01/70299 | 9/2001 |
| WO | 01/74273 | 10/2001 |
| WO | 01/89409 | 11/2001 |
| WO | 02/00138 | 1/2002 |
| WO | 02/053066 | 7/2002 |
| WO | 02/068012 | 9/2002 |
| WO | 03/007842 | 1/2003 |
| WO | 03/055414 | 7/2003 |
| WO | 03/063924 | 8/2003 |
| WO | 2004/026174 | 4/2004 |
| WO | 2004/026180 | 4/2004 |
| WO | 2005/009295 | 2/2005 |
| WO | 2005/014077 | 2/2005 |
| WO | 2006/028925 | 3/2006 |
| WO | WO 2006/127127 | 11/2006 |

OTHER PUBLICATIONS

Nakamura M.D., Shigeru, "Techniques for Palmaz-Schatz Stent Deployment in Lesions with a Large Side Branch," *Catheterization and Cardiovascular Diagnosis*, vol. 34, pp. 353-361 (1995).

Caputo, Ronald P., "Stent Jail: A Minimum-Security Prison," *The American Journal of Cardiology*, vol. 77, pp. 1226-1230 (Jun. 1, 1996).

Colombo, M.D., Antonio, ""Kissing" Stent for Bifurcational Coronary Lesion," *Catheterization and Cardiovascular Diagnosis*, vol. 30, pp. 327-330 (Dec. 1993).

Carrie, M.D., Didier, ""T"-Shaped Stent Placement: A Technique for the Treatment of Dissected Bifurcation Lesions," *Catheterization and Cardiovascular Diagnosis*, vol. 37, pp. 311-313 (Mar. 1996).

Katoh, M.D., Osamu, "New Double Wire Technique to Stent Ostial Lesions," *Catheterization and Cardiovascular Diagnosis*, vol. 40, pp. 400-402 (Apr. 1997).

Lewis, M.D., Bruce E., "Acute procedural results in the treatment of 30 coronary artery bifurcation lesions with a double-wire atherectomy technique for side-branch protection," *American Heart Journal*, vol. 127:6, pp. 1600-1607 (Jun. 1994).

Yamashita, M.D.,PhD., Takehiro, "Bifurcation Lesions: Two Stents Versus One Stent—Immediate and Follow-up Results," *Journal of the American College of Cardiology*, vol. 35:5, pp. 1145-1151 (Apr. 2000).

Satler, M.D., Lowell F., "Bifurcation Disease: to Treat or Not to Treat," *Catheterization and Cardiovascular Interventions*, vol. 50, pp. 411-412 (2000).

U.S. Appl. No. 09/663,111, filed Sep. 15, 2000, Davidson et al.
U.S. Appl. No. 09/614,472, filed Jul. 11, 2000, Davidson et al.
U.S. Appl. No. 09/235,996, filed Jun. 4, 1999, Vardi et al.

\* cited by examiner

BALLOON FOLD DESIGN FOR DEPLOYMENT OF BIFURCATED STENT PETAL ARCHITECTURE

CROSS-REFERENCE TO RELATED APPLICATIONS

Not Applicable

STATEMENT REGARDING FEDERALLY SPONSORED RESEARCH

Not Applicable

BACKGROUND OF THE INVENTION

1. Field of the Invention

In some embodiments this invention relates to implantable medical devices, their manufacture, and methods of use. Some embodiments are directed to delivery systems, such as catheter systems of all types, which are utilized in the delivery of such devices.

2. Description of the Related Art

Balloon catheters are employed in a variety of medical procedures. One such procedure is angioplasty which is a well known medical practice used in the treatment of diseased arteries in the vasculature of a patient. Using angioplasty procedures, alone, however, involves a risk of restenosis of the artery, which may necessitate another angioplasty procedure, a surgical bypass procedure, or some method of repairing or strengthening the area. Therefore, it has become more common practice to use a catheter-delivered stent to prevent restenosis and to reinforce and strengthen weakened vessel walls.

A stent is a medical device introduced to a body lumen and is well known in the art. Stents, grafts, stent-grafts, vena cava filters, expandable frameworks, and similar implantable medical devices, collectively referred to hereinafter as stents, are radially expandable endoprostheses which are typically intravascular implants capable of being implanted transluminally and enlarged radially after being introduced percutaneously. Typically, a stent is implanted in a blood vessel at the site of a stenosis or aneurysm endoluminally, i.e. by so-called "minimally invasive techniques" in which the stent in a radially reduced configuration, optionally restrained in a radially compressed configuration by a sheath and/or catheter, is delivered by a stent delivery system or "introducer" to the site where it is required. The introducer may enter the body from an access location outside the body, such as through the patient's skin, or by a "cut down" technique in which the entry blood vessel is exposed by minor surgical means.

After being introduced percutaneously, stents can be expanded by an internal radial force, such as when mounted on an inflatable balloon. Stents can also be self-expanding or a combination of self-expanding and balloon expandable (hybrid expandable). Stents may be implanted to prevent restenosis following angioplasty in the vascular system. Stents may be expanded and implanted in a variety of body lumens or vessels such as within the vascular system, urinary tracts, bile ducts, fallopian tubes, coronary vessels, secondary vessels, etc.

A number of complications arise when stenoses form at vessel bifurcation sites. A bifurcation site is an area of the vasculature or other portion of the body where a first (or parent) vessel is bifurcated into two or more branch vessels. Where a stenotic lesion or lesions form at such a bifurcation, the lesion(s) can affect only one of the vessels (i.e., either of the branch vessels of the parent vessel) two of the vessels, or all three vessels. One complication involves irregular folding of the balloon or balloon portion which pushes against and moves that portion of the stent which expands into the vessel bifurcation. While auxiliary portions of a delivery system have been successful in expanding portions of stents into a side branch vessel, there remains a need for devices that are particularly suitable for expanding stents at a bifurcation to achieve an ideal expanded configuration.

The art referred to and/or described above is not intended to constitute an admission that any patent, publication or other information referred to herein is "prior art" with respect to this invention All US patents and applications and all other published documents mentioned anywhere in this application are incorporated herein by reference in their entirety.

Without limiting the scope of the invention a brief summary of some of the claimed embodiments of the invention is set forth below. Additional details of the summarized embodiments of the invention and/or additional embodiments of the invention may be found in the Detailed Description of the Invention below.

BRIEF SUMMARY OF THE INVENTION

This invention contemplates a number of embodiments where any one, any combination of some, or all of the embodiments can be incorporated into a stent and/or a stent delivery system and/or a method of use. The present invention relates to novel folding arrangement for inflation balloons. The inflation balloons are folded in a systematic pattern which aids in the proper deployment of the side branch assembly of the stent. In particular, the improved folding arrangement aids in the deployment of the extending members relative to the bifurcated vessel wall. These and other aspects of the invention are set forth below.

At least one embodiment of the invention is directed to a balloon catheter comprising a balloon inflation system. The balloon inflation system has a side branch balloon structure capable of at least partially expanding a side branch structure of a bifurcated stent. When in an un-inflated configuration, the side branch balloon structure is folded in a pattern which permits orderly unfolding when the side branch is inflated. Contemplated embodiments include a main branch balloon structure capable of inflating a main tubular body of a bifurcated stent which is either in or not in fluid communication with the side branch balloon structure.

At least one embodiment of the invention is directed to a side branch balloon structure comprising a radial end, a luminal end, and a side portion extending between the radial and luminal ends. When in the inflated configuration, the radial end is further away from the main branch central axis than the luminal end, and when in the un-inflated configuration the radial and luminal ends are substantially adjacent to each other. When in the un-inflated configuration, the side branch balloon structure can be folded such that: at least some of the side portion lies flush against and over the radial end, at least some of the side portion is further folded into pleats, and/or at least some of the side portion is further folded into overlapping folds. The side portion can also be folded such that: it is folded into three or more segments with overlapping regions between the folded segments, at least one segment lies above one overlapping region and beneath one overlapping region, every folded segment lies above one overlapping region and beneath one overlapping region, at least some of the overlapping folds are of different sizes, at least some of the pleats are of different sizes, and/or the pattern is generally uniform about a side branch axis.

At least one embodiment of the invention is directed to a balloon catheter further comprising a catheter shaft disposed about which is a bifurcated stent. The bifurcated stent has a main tubular body and a side branch structure having an iris and a crown configuration. When in the crown configuration at least a portion of the side branch assembly defines a fluid lumen in fluid communication with main tubular body and extends away from the main tubular body at an oblique angle. When in the iris configuration at least a portion of the side branch assembly is positioned adjacent to the orderly folded side branch balloon structure. The side branch assembly can also comprise one or more petals which when crowned define at least a portion of the second fluid lumen. The folded pattern results in the positioning of smooth portions of the side branch balloon structure against the petals. These smooth portions can be without folds and can cause a portion of the side branch balloon structure to inflate in a sweeping rotational motion. In addition, the pattern can allow for at least a portion of the side branch balloon structure to inflate by first primarily expanding in a circumferential direction away from a center of the side branch balloon structure and later primarily expanding in a radial direction.

At least one embodiment of the invention is directed to a method of folding a side branch balloon structure comprising the steps of: forming a cup by folding a radial end of the a side branch balloon structure into a luminal end of the side branch balloon structure and forming a discus by smoothly folding down the most radial portion of the cup against the radial end of the side branch balloon structure. The method can further including the steps of: inflating the side branch balloon, deflating the side branch balloon, and crimping an unexpanded side branch assembly of an unexpanded bifurcated stent over the folded side branch balloon structure.

BRIEF DESCRIPTION OF THE SEVERAL VIEWS OF THE DRAWINGS

The invention is best understood from the following detailed description when read in connection with accompanying drawings, in which.

DETAILED DESCRIPTION OF THE INVENTION

Figure 1:
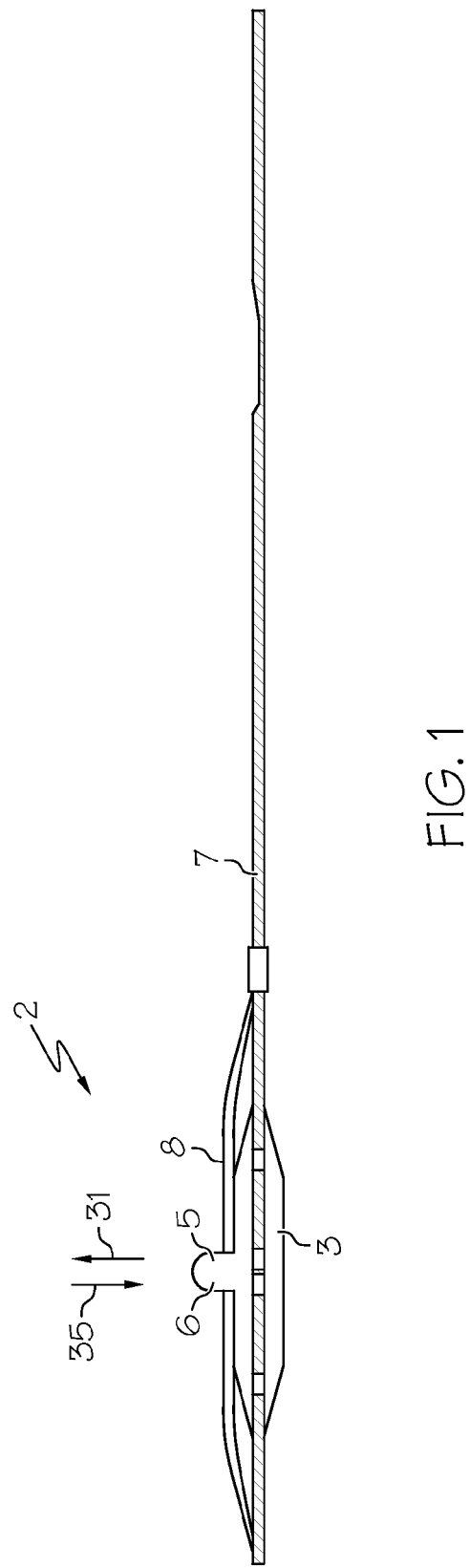
FIG. 1 is a cross sectional perspective view of an inflated bifurcating balloon on a balloon catheter.

The invention will next be illustrated with reference to the figures wherein the same numbers indicate similar elements in all figures. Such figures are intended to be illustrative rather than limiting and are included herewith to facilitate the explanation of the apparatus of the present invention.

For the purposes of this disclosure, like reference numerals in the figures shall refer to like features unless otherwise indicated.

Depicted in the figures are various aspects of the invention. Elements depicted in one figure may be combined with, or substituted for, elements depicted in another figure as desired.

Figure 2:
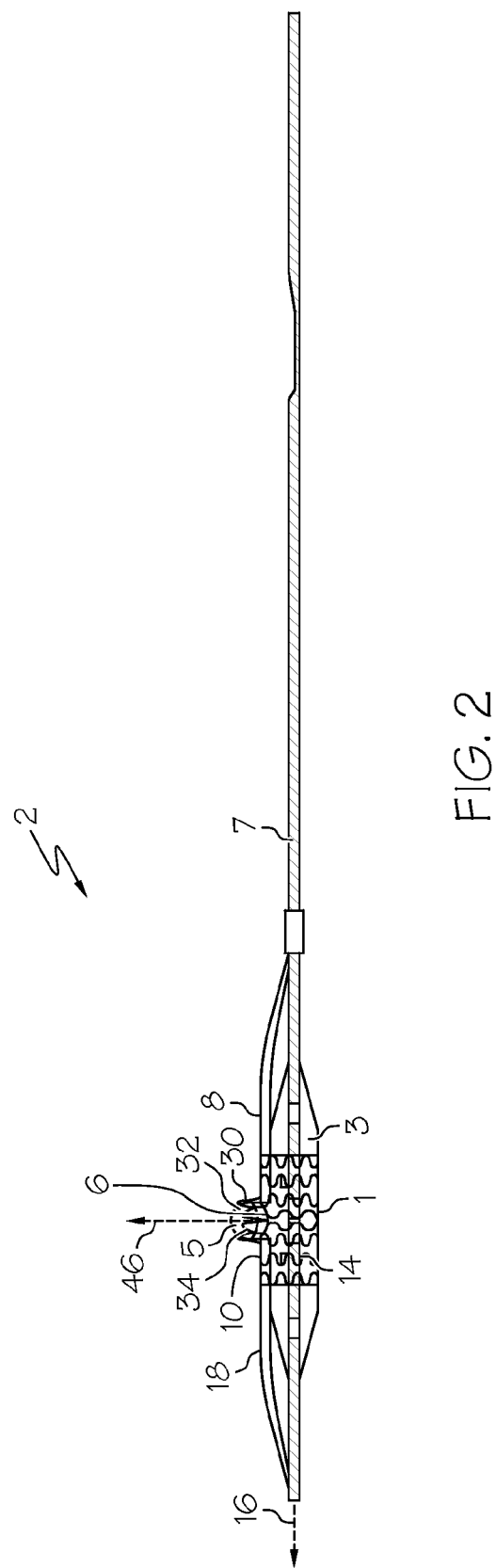
FIG. 2 is a schematic perspective view of an expanded bifurcated stent on a balloon catheters.

Embodiments of the invention are directed to folding arrangements of both multiple lumen type and single lumen type balloon catheters. Referring now to FIG. 1, there is shown a multiple balloon type catheter (2) along whose main catheter shaft (7) is an expanded side balloon structure (5). FIG. 2 shows disposed about the inflated side balloon structure (5) and the inflated main catheter balloon (3) a bifurcated stent (1) in an expanded state. Some examples of multiple lumen catheters are discussed in published US Patent Publication Nos. US 2003/0163082, US 2005/0015108A1, and US 2005/0102019A1 and co-pending, concurrently filed, and commonly owned U.S. Application having an Ser. No. 11/508,692 the entire disclosure of which are incorporated herein by reference in their entirety. The multiple lumen type balloon catheter (2) comprises at least two balloons. One is the main catheter balloon (3) and the other is the side branch balloon (6). The side branch balloon (6) comprises a side balloon structure (5) in fluid communication with a side inflation lumen (8).

Some examples of single balloon type balloon catheters are discussed in published US Patent Publication No. US 2004/0138737 A1 the entire disclosure of which is incorporated herein by reference in its entirety. In a single balloon type balloon catheter, integrated into the material of the main catheter balloon is a blister of bulge which defines the side balloon structure (5). As the main catheter balloon is inflated, its side balloon structure (5) inflates as well.

Referring again to FIG. 2 it is shown that the stent (1) comprises two portions, a generally tubular main stent body (10) which defines a primary fluid lumen (14) and a side branch assembly (30). The stent (1) has an expanded and an unexpanded state. When in the expanded state, the stent (1) assumes a greater volume than when in the unexpanded state. The main stent body or main branch (10) of the bifurcated stent (1) extends about a main branch central axis (16). The main stent body (10) can be expanded by pressure applied to the inner surface of the main stent body (10) by the inflation of the main catheter balloon (3), it can be inflated by a self-expansion mechanism, or it can be expanded by some combination of the two.

When the stent (1) is in the expanded state, the side branch assembly or side branch (30) forms a bifurcating side branch which defines a secondary fluid lumen (34) in fluid communication with the primary fluid lumen (14). The side branch assembly extends about a side branch axis (46). This side branch is capable of extending in a radial direction (31) out of the parent vessel and into the branch vessel. In at least one embodiment, the side branch assembly (30) comprises one or more petals (32). For purposes of this application the definition of the term "petal" is one or more side branch members capable of twisting, bending, pivoting or otherwise opening to define the second fluid lumen (34) by opening away from the tubular shape defined by the generally tubular structure of the outer surface of the first stent body (10). It will be appreciated by persons of ordinary skill in the art that side branch assemblies can also comprises non-petal structures. As a result, all embodiments in this application which describe petals will be understood to contemplate non-petal type side branch assemblies as well.

The petals (32) can be arranged in an iris configuration when the stent (1) is unexpanded and in a crown configuration when the stent (1) is expanded. For purposes of this application the definition of the term "iris" is when one or more petals (32) are generally lying along the tubular shape defined by the generally tubular structure of the outer surface of the first stent body (10) and are covering at least a portion of a side branch opening (18) in the main stent body (10). For purposes of this application the definition of the term "crown" is when as at least one petal (32) are positioned at an oblique angle radially displaced from the tubular shape defined by the generally tubular structure of the outer surface of the first stent body (10). For the purposes of this application, the definition of the term "oblique" is an angle of greater than zero degrees, such as an angle of between about 1 and about 180 degrees. An oblique angle explicitly includes angles of both exactly and about 90 degrees. The petals (32) are pushed from the iris configuration into the crown configuration at least in part by pressure applied to the inner surface of the petals (32) by the inflation of the a side balloon structure (5).

Figure 3:
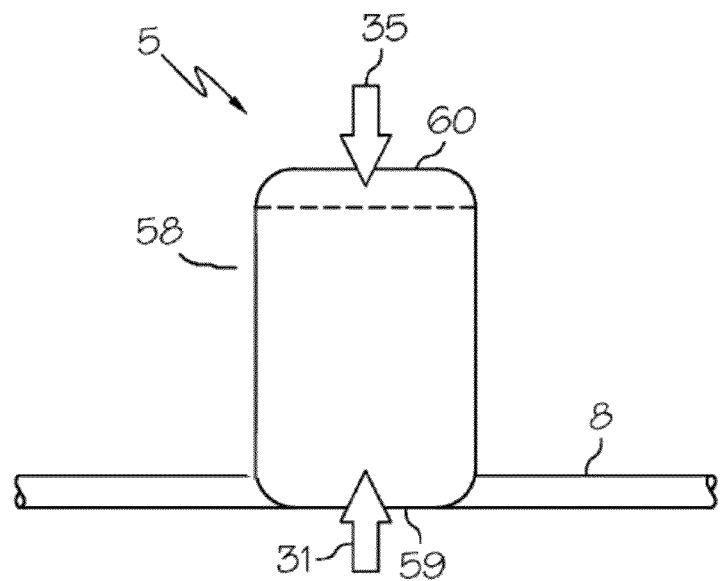
FIG. 3 is a cross sectional schematic view of a bifurcating balloon.
Figure 4:
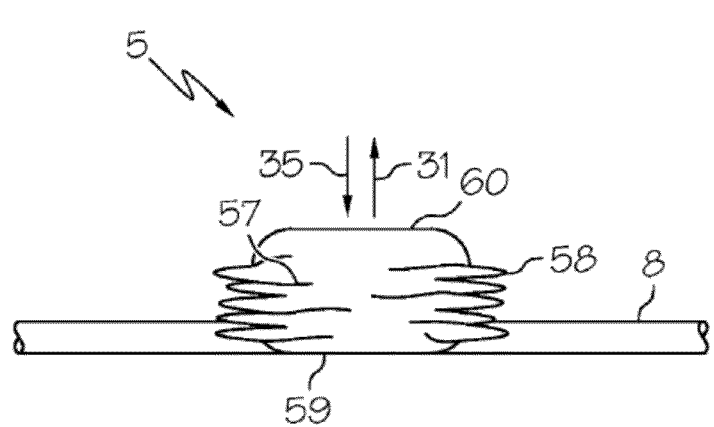
FIG. 4 is a cross sectional schematic view of a bifurcating balloon which is irregularly compressed, illustrative of a prior art method.

FIGS. 3 and 4 are illustrative of a prior art folding technique. Before expansion, when in the unexpanded state, the side balloon structure (5) is in an un-inflated configuration. When this un-inflated configuration is the result of deflation and/or the application of a generally untargeted force in the luminal (towards the stent lumen) direction (35) or one or more generally untargeted forces along at least a portion of the radial end (60), the luminal end (59), and/or the side (58) of the side balloon structure (5) (as shown in FIG. 3), the un-inflated balloon assumes an irregular shape. As FIG. 4 illustrates, simple compressive force causes the balloon folds (57) and the overall assumed shape to be randomly formed due to the inconsistent and random buckling and pleating that takes place within the balloon material. Only a small portion if any of the inner surface of the radial end (60) and the inner surface of the luminal end (59) of the side (58) come into direct contact with each other and are separated by material from other portions of the side balloon structure.

Figure 6:
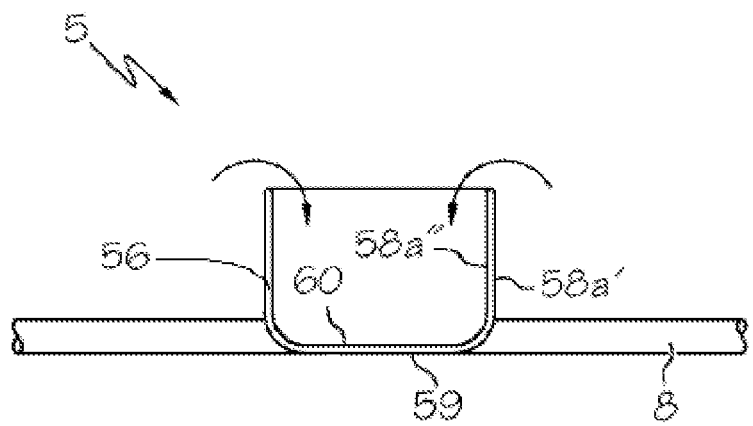
FIG. 6 is a cross sectional schematic view of a bifurcating balloon of FIG. 5 after folding into a cup configuration.
Figure 9:
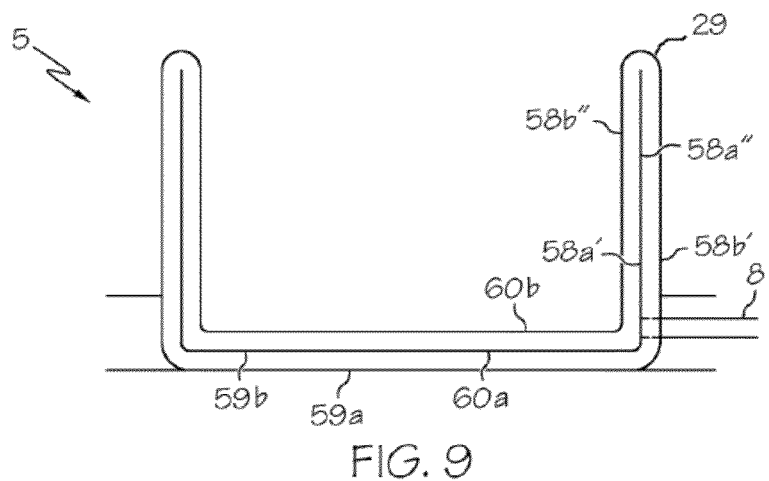
FIG. 9 is a cross sectional schematic view of a bifurcating balloon as in FIG. 8 that has been folded into a cup configuration.
Figure 12:
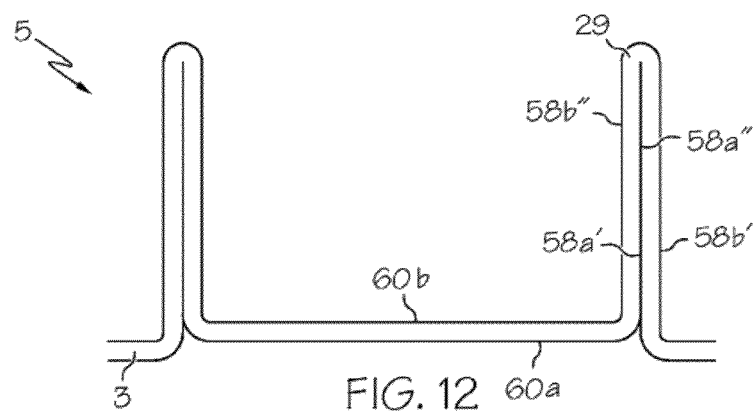
FIG. 12 is a cross sectional schematic view of a bifurcating balloon in a single lumen type inflation assembly as in FIG. 11 that has been folded into a cup configuration.

In at least one embodiment of the invention, the side balloon structure (5) when in the unexpanded state is configured according to an organized arrangement. Referring now to FIG. 6 there is shown a first step of preparing one such organized arrangement, the "cup" arrangement. When the side balloon structure (5) is in the cup arrangement, at least a portion of the inner surface of the radial end (60a) and the inner surface of the luminal end (59) are substantially flush with one another. Similarly at least a portion of the inner side of the upper ends of the side lengths (58a") and the inner side of the lower ends of the side lengths (58a') are also substantially flush with one another. The cup arrangement is characterized by a folded interface (56) being formed between the upper and lower ends of the side balloon structure. FIG. 9 illustrates the cup arrangement in a dual lumen type balloon catheter and FIG. 12 illustrates the cup arrangement in a single lumen type balloon catheter.

Figure 5:
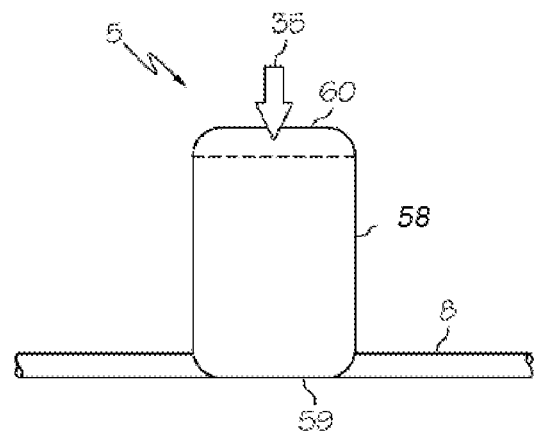
FIG. 5 is a cross sectional schematic view of a bifurcating balloon being systematically folded.

As illustrated in FIG. 5, in at least one embodiment, the cup arrangement is formed by the application of a compressive force in the luminal direction (35) evenly distributed along the entirety of the radial end (60) and vectored towards the luminal end (59). This force can be applied in combination with a mandrel which keeps the side lengths (58) straight and rigid. This applied force will cause a folded interface to form between that portion (58a") of the side length (58) that is pushed internal to the inner side of the lower ends of the side lengths and that portion (58a) which remains external to the inner side of the lower ends of the side lengths. As portions of the side length (58) are pushed internal to form the cup, a lip (29) forms. See also FIGS. 9 and 12.

In at least one embodiment the cup arrangement is formed by the application of a luminally directed (35) force focused towards the center of the radial end (60) of the side balloon structure (5). This focused force cooperates with a side directed force that pushes that portion of the upper end of the balloon material internal to the inner side of the lower ends of the side lengths (58a') to be flush with the inner side of the lower ends of the side lengths (58a'). The side balloon structure (5) can folded while, before, or after the main stent body inflating balloon or balloon portion is inflated or collapsed.

Figure 10:
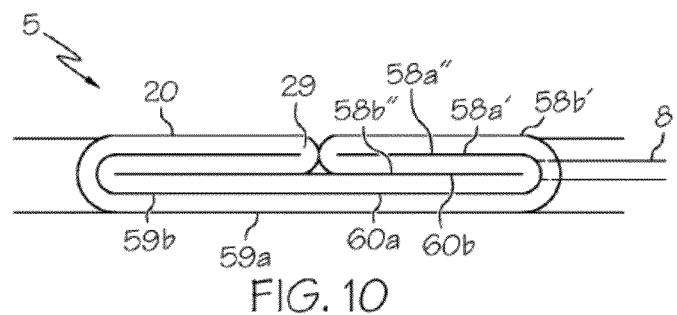
FIG. 10 is a cross sectional schematic view of a bifurcating balloon folded into a discus configuration from a cup configuration as illustrated in FIG. 9.
Figure 11:
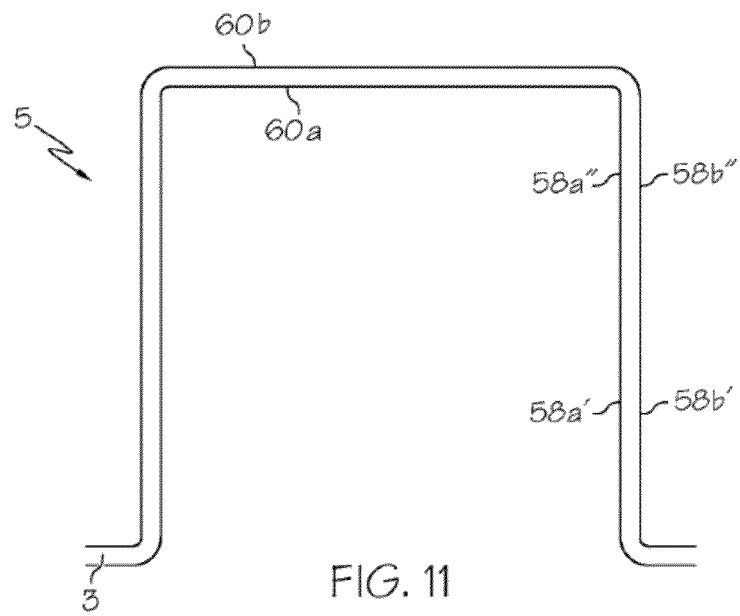
FIG. 11 is a cross sectional schematic view of an inflated bifurcating balloon in a single lumen type inflation assembly.

Referring now to FIG. 10 there is shown at least one embodiment of the invention where at least some of the upper ends of the side lengths (58a" and 58b") and lower ends of the side lengths (58a' and 58b') are folded according to a "discus" arrangement. The discus arrangement can be cooperative with a cup arrangement or independently arranged. In a discus arrangement, at least a portion of the outer surface of the upper end of the side length (58b") is folded in such a manner that it lies flush against the outer surface of the radial end (60b).

Figure 7:
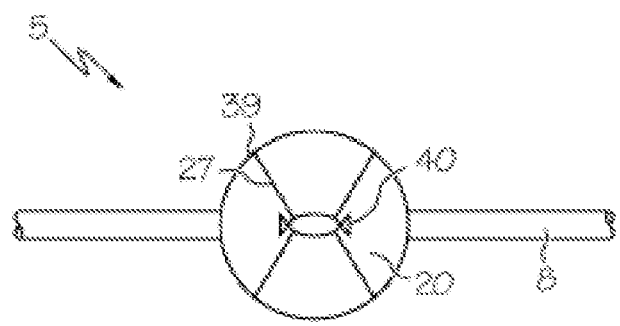
FIG. 7 is an overhead view cross sectional schematic view of a bifurcating balloon systematically folded from a cup configuration as illustrated in FIG. 6.
Figure 8:
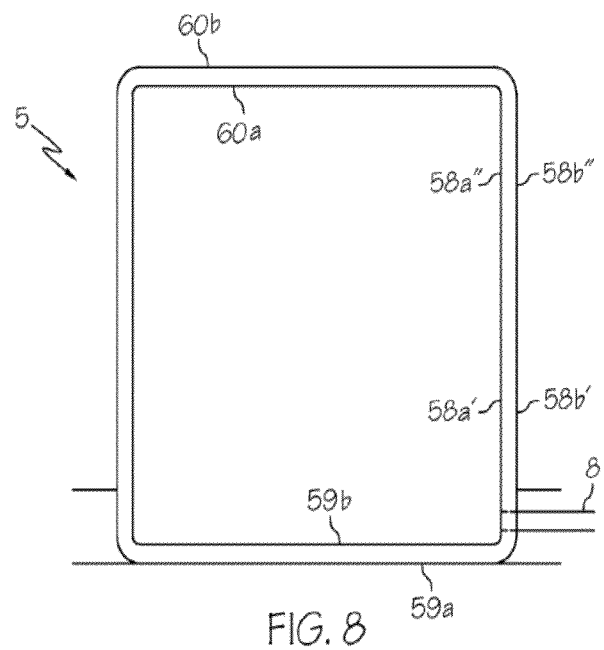
FIG. 8 is a cross sectional schematic view of an inflated bifurcating balloon in a dual lumen type inflation assembly.
Figure 13:
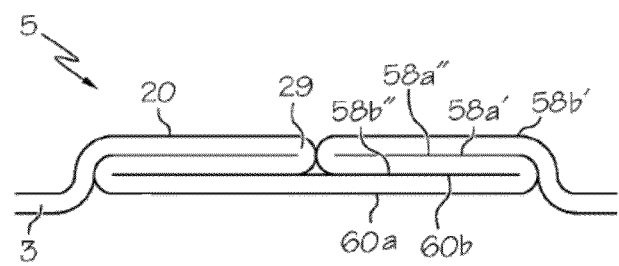
FIG. 13 is a cross sectional schematic view of a bifurcating balloon in a single lumen type inflation assembly systematically folded into a discus configuration systematically folded from a cup configuration as illustrated in FIG. 12.

In at least one embodiment illustrated in FIG. 7, the discus arrangement in the side balloon structure (5) has generally organized arrangement of pleats (40) in the folded balloon material. These pleats (40) can be evenly spaced about the compressed side balloon structure (5). Because those portions of the balloon material closer to the center of the side balloon structure (5) have less area for their material to be spread about, the pleats (40) are present in portions of the balloon material closer to the center of the side balloon structure (5). Referring now to FIGS. 10 and 13, it can be understood because the pleats allow for overlap of balloon material in the smaller central region of the side balloon structure (5) in the discus arrangement, they can be located at or near the lip (29) between the upper and lower ends of the side length of the side balloon structure (5).

Figure 14:
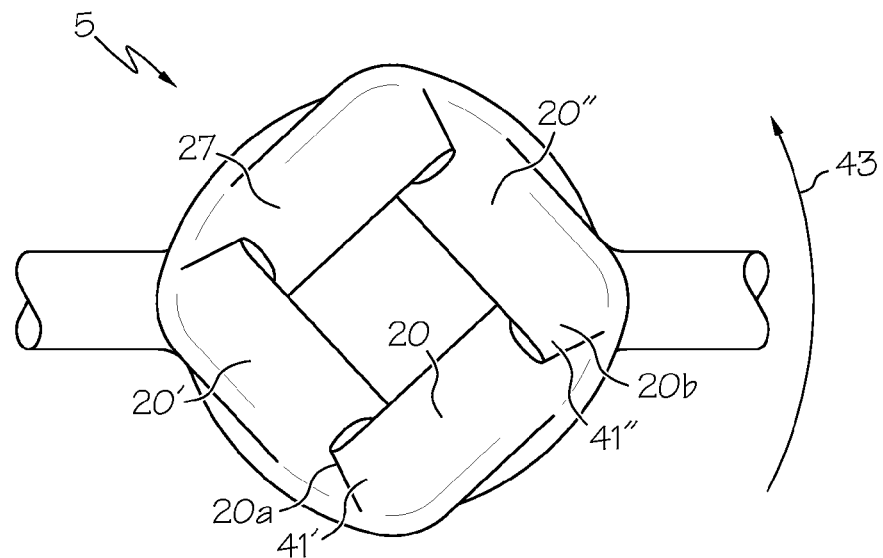
FIG. 14 is a detailed overhead schematic view of a systematically folded bifurcating balloon.
Figure 15:
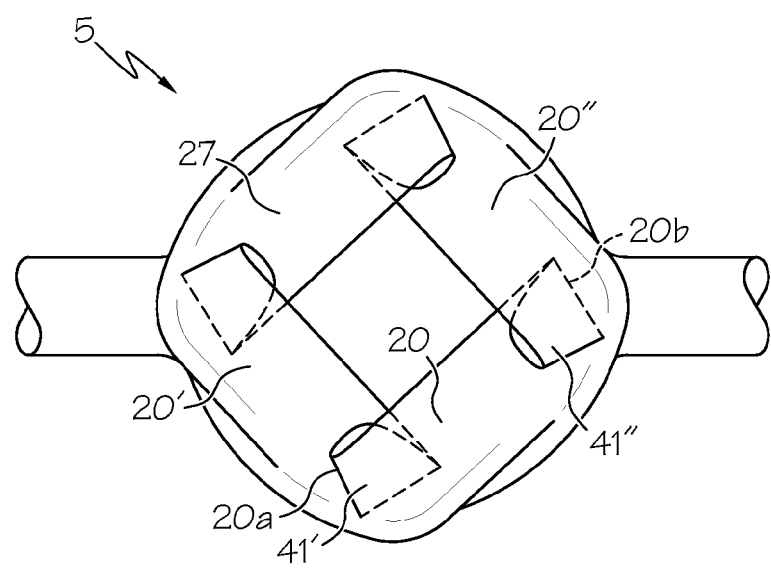
FIG. 15 a detailed cross sectional overhead schematic view of a systematically folded bifurcating balloon.

In at least one embodiment illustrated in FIGS. 14 and 15, at least a portion of the side balloon structure (5) is in a discus arrangement where the overlapping folds of material (27) are in an inter-layered arrangement FIG. 14 illustrates a top down view of this structure and FIG. 15 delineates with phantom lines the covered folded segments of balloon material (20). For purposes of this application, the term inter-layered is defined as an arrangement in which one side of an object is positioned above the adjacent side of a first adjacent object and the other opposite side of the object is positioned below the adjacent side of a second adjacent object. FIGS. 14 and 15 illustrate a segment (20) of the compressed side balloon structure (5) where the portion of a first end (20a) in a first overlapping region (41') is positioned above the material of at least one adjacent folded segment (20') and a second end (20b) overlapping region (41') is positioned below the material of at least one adjacent folded segment (20"). The inter-layered arrangement provides at least two advantages. First during inflation as each segment is pushed in a radial direction, each inter-layered segment radially pushes the adjacent segment reducing the overall energy needed to radially push all of the segments. Secondly while inflating, the arrangements cause the segments to move in a rotational direction (43). This rotational direction (43) provides a precisely directed pushing force against the crowning side branch assembly, and by sweeping each of the petals in a different tangential direction, reduces the likelihood of petals colliding with each other when crowning. The phantom lines in FIG. 15 shown at least one embodiment where the overlapping regions (41) become progressively smaller the further they are from the center of the side balloon structure (5).

Figure 16:
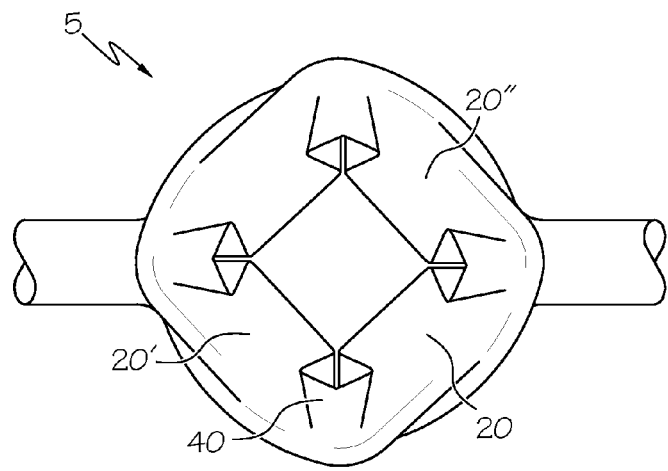
FIG. 16 is a detailed overhead schematic view of a systematically pleated bifurcating balloon.
Figure 17:
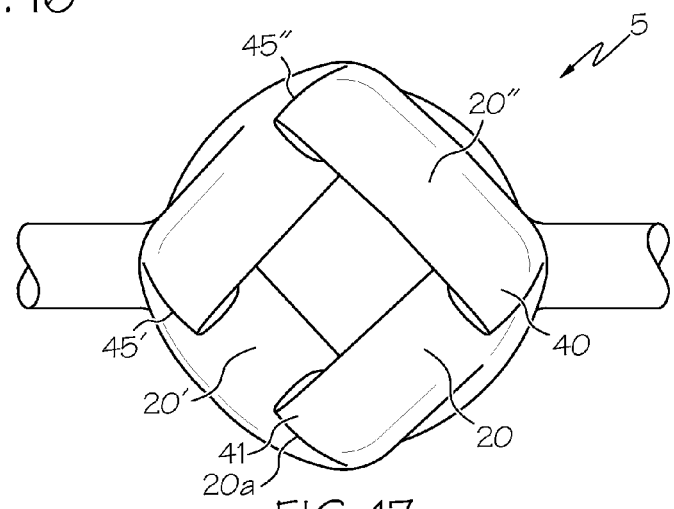
FIG. 17 is a detailed overhead schematic view of a systematically folded and pleated bifurcating balloon.
Figure 18:
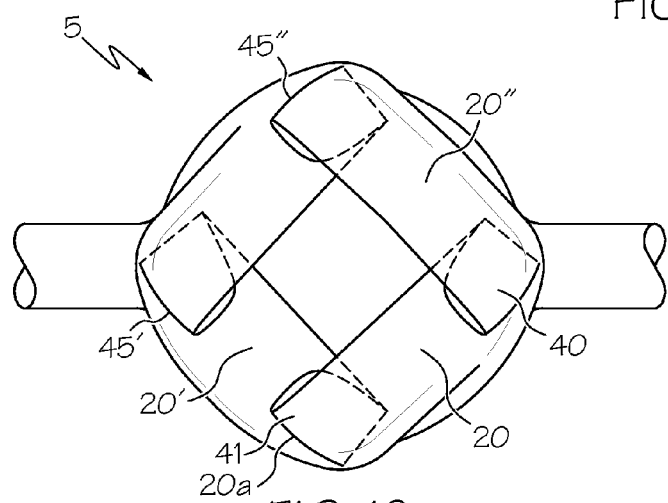
FIG. 18 is a detailed overhead cross sectional schematic view of a systematically folded and pleated bifurcating balloon.

Referring now to FIG. 16 there are shown an embodiment in which the discus arrangement features a plurality of evenly spaced pleats (40). The evenly spaced pleats (40) when inflated at least partially push the petals in different direction reducing the likelihood of petal collisions. FIGS. 17 and 18 illustrate embodiments having combinations of the features of FIGS. 14 and 16. FIGS. 17 and 18 show both one or more pleats (40) and one or more folded overlapping regions (41). In addition they show that if one segment (20) of balloon material has a highly overlapping region at one end (45") it can also have a less overlapping region (45') at the other end of that segment. Modifying the degree of overlap at different segment ends allows for modulation in the rotational sweep and speed with which different portions of the side balloon structure (5) will attain during inflation. Such modulation facilitates expansion of irregularly shaped side branch structures.

The various flush and even folding arrangements impart a number of advantages to the inflation process of the side balloon structure (5). One advantage is that the folding arrangement allows for control over the sequence of the inflation of particular portions of the side balloon structure allowing forces to be applied in a desired sequence. Another advantage is that they allow for the smooth and even expansion of the outer surface of the radial end (60b) as it moves radially (31) away from the luminal end (59). Also, the organized unfolding that the side balloon undergoes has a predictable sweeping motion which is cooperative with the crowning motion of the petals. This predictable sweeping motion reduces or prevents shear forces which can be caused by erratic motion that accompanies the inflation induced smoothing out of erratically shaped fold lines and erratically positioned portions of the side balloon structure (5). The sweeping motion with which the organized folds and pleats unfold when expanded also reduces wasted inflation energy that would otherwise accompany untangling and untwisting erratically positioned portions of the side balloon structure (5). The organized folding designs are also repeatable and can be easily integrated into industrial production lines. In addition, the organized structures reduce the likelihood of unwanted volume producing voids occupying the side branch structure (5) reducing its overall profile. Similarly, the flush and even folding arrangements when inflated allow for an increase in side balloon structure (5) volume at a uniform or predictable rate volume which reduces rapid fluctuations in the velocity of the balloon inflation which would otherwise accompany the inflation of dissimilarly folded portions.

The organized arrangement also allows for application of precise pushing force to be applied by the outer surface of the radial end (60b) against the petals. This precise pushing force increases inflation efficiency by assuring that majority of the volumetric expansion can be harnessed to crown the side branch assembly. FIGS. 19-23 illustrate one embodiment in which the precise pushing force is applied efficiently to petals (32), other portions of the side branch assembly (30), other portions of the balloon, of any other object positioned over the side balloon structure (5)

Figure 19:
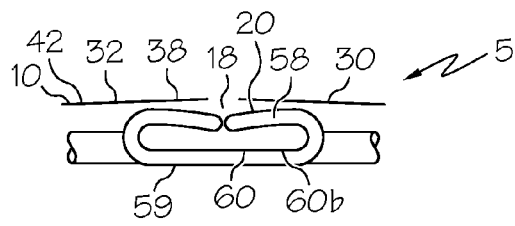
FIG. 19 is a cross sectional schematic view of a systematically folded bifurcating balloon beneath a stent side branch assembly.

In FIGS. 19-23 there is shown at least one embodiment of a side balloon structure (5) having a cup and discus arrangement where the blunt unfocused radial force that the inflation of the side balloon structure (5) of FIG. 4 would produce is replaced by an orderly, sequential, and precisely directed series of forces. When the side balloon structure (5) inflates, first the discus arrangement at least partially unfolds, after which the cup arrangement is rearranged as the balloons volume is increased. As shown in FIG. 19, prior to inflation, the folded side balloon structure (5) has a low cross sectional profile. Although FIG. 19 illustrates a volume void between the folded side lengths equal to the volume of the lengths it will be understood that significantly greater or lesser void volumes are contemplated by this invention.

Figure 20:
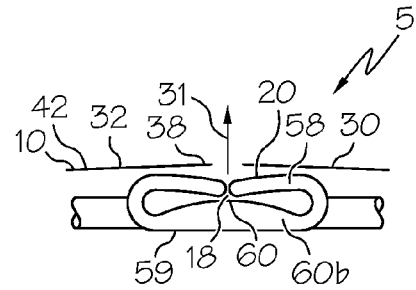
FIG. 20 is a cross sectional schematic view of a systematically folded bifurcating balloon beneath a stent side branch assembly with a bulging radial end.
Figure 21:
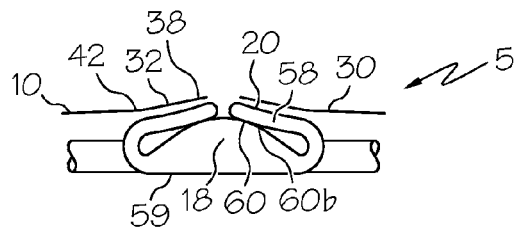
FIG. 21 is a cross sectional schematic view of a systematically folded bifurcating balloon beneath a stent side branch assembly with a bulging radial end that is crowning the side branch assembly.
Figure 22:
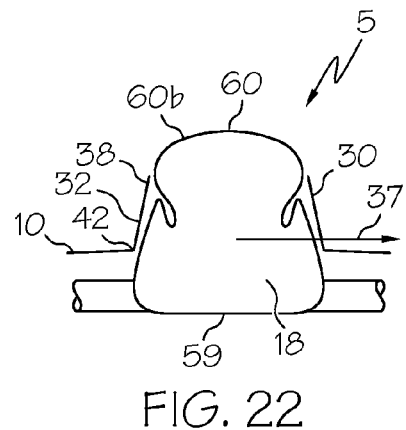
FIG. 22 is a cross sectional schematic view of a systematically folded bifurcating balloon which has reversed its cup configuration.
Figure 23:
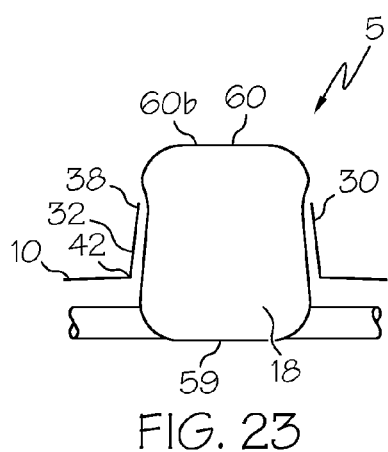
FIG. 23 is a cross sectional schematic view of an inflated systematically folded bifurcating balloon about which is disposed a crowned sent side branch assembly.

As illustrated in FIG. 20 and temporally subsequent FIG. 21, when the side balloon structure (5) begins its inflation, the outer surface of the radial end (60b) bulges radially before other portions of the side balloon structure (5). As shown in FIGS. 21 and 22, this initial bulging applies a controlled radially directed pressing force against the folded side lengths (58). The radially directed pressure pushes the side lengths in a sweeping path complimentary to the bending or twisting motions that the petals (32) will undergo as they transition from an iris to a crown configuration. In particular, because the radial bulge (36) is more luminal at its center than an its edges, the radial bulge (36) applies more pushing force against the petal summit (38) and less against the petal base

(42) providing torque which is highly cooperative to the bending and twisting motion needed for successful crowning.

Because the folding arrangement, limits the allowed initial motions to the side lengths (58) in an outwardly directed arced path there is a greatly reduced amount of friction, rubbing or chaffing between the petal and the unfolding side balloon structure (5). In addition, because the petals (32) begin to bend outward (and away from majority of the mass of the side branch structure(5)) at the very beginning of the inflation process, the likelihood of an erratic motion by a portion of the balloon deforming, distorting, or otherwise improperly extending the side branch assembly becomes reduced. Lastly because the initial inflation process moves the petals, the petals develop outwardly directed momentum which reduces the overall energy needed to extend the petals (32).

Referring now to FIG. 22 there is shown that after the discus arrangement becomes somewhat unfolded the cup arrangement then becomes unfolded as well. The radially directed (31) force described in FIGS. 19, 20, and 21 declines and is replaced by outward a force directed in outward directions (37) parallel to axes extending from the center of the side opening (18) to the main stent body (10). This gradual replacement of the radially directed force with the outwardly directed force is complimentary to the direction vector of the petals as they gradually transition from a substantially iris configuration to a substantially crowned configuration. Because as the petals become more crowned the petal tips (38) arc from a primarily radial trajectory (31 of FIG. 20) to a primarily outward trajectory (37) the sequence of inflation matches the motion of the petals resulting in highly efficient inflation system.

Referring now to FIG. 19, in at least one embodiment, to facilitate the inflation properties of the side balloon structure (5), the radial side (60) is thinner than (60) the side length (58). By folding the side balloon structure (60) into discus arrangements, the thicker of the materials abuts the side branch assembly (30) reducing the likelihood that a portion of balloon will be ruptured or otherwise damaged by impacting against the side branch assembly (30).

Figure 24:
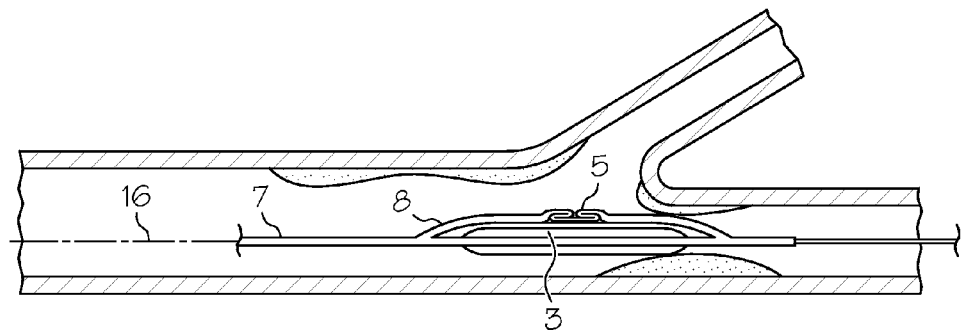
FIG. 24 is a cross sectional schematic view of an unexpanded bifurcating balloon catheter system positioned within a bifurcation site.
Figure 25:
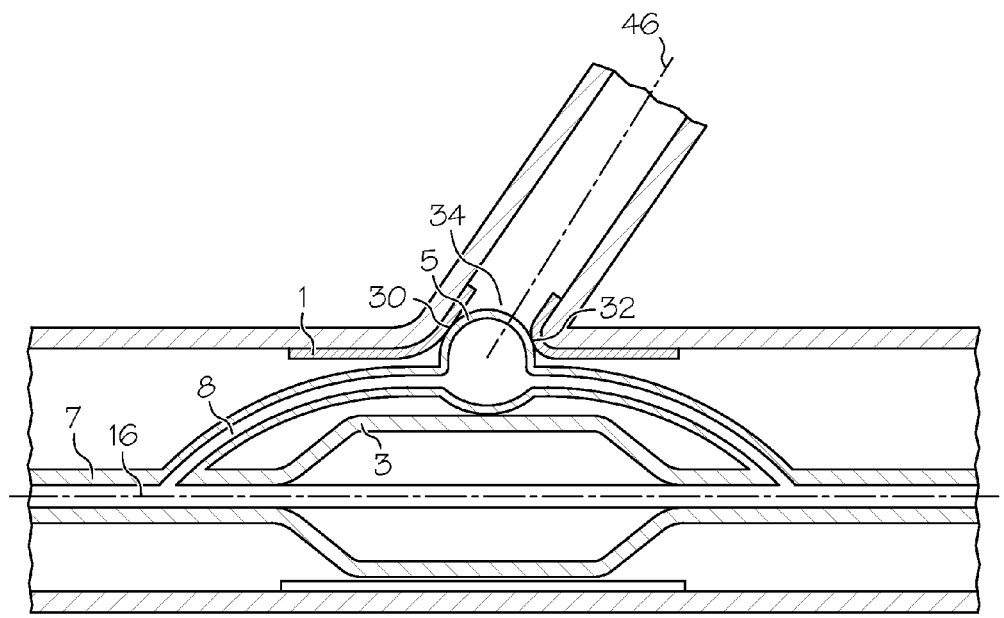
FIG. 25 is a cross sectional schematic view of an expanded bifurcating balloon catheter system which has deployed a stent within a bifurcation site.

Referring now to FIGS. 24 and 25 there is shown the main catheter balloon (3) and the side balloon structure (5). The main catheter balloon (3) and the side balloon structure (5) are in fluid communication which allows the main catheter balloon (3) and the side balloon structure (5) to undergo common inflation and deflation. FIG. 24 illustrates a balloon catheter (2) in the unexpanded state and FIG. 25 in the expanded state These figures also show inflation lumens at the distal and proximal sides of the side balloon structure (5) which can apply inflating fluid to different portions of the folded side balloon structure (5).

Embodiments contemplated by this invention include catheters in which the main catheter balloon (3) and the side balloon structure (5) are linked to different fluid sources which allows them to undergo independent inflation and deflation. Similarly two or more inflation lumens can be positioned at locations about the side balloon structure (5). These inflation lumens need not only be distal to or proximal to the side balloon structure and can be positioned above, below, or at any position around the side balloon structure (5). Depending on the desired sequences of inflation, the catheter may be configured so that each inflation lumen can be independently filled. Alternatively the inflation lumens may be configured to be in common fluidic communication with one or more of the other inflation lumens. In addition one or more inflation lumens may be independent to provide for the withdrawal of fluid from the side balloon structure (5) or may utilize valves to only allow fluid to pass once a desired pressure level is present within the side balloon structure (5) and/or within the inflation lumen.

Coordination of the order of inflation, inflation pressure, fluid flux, and fluid flow directions can be combined with the other inflation embodiments disclosed in this application to facilitate the efficient and successful inflation of the side balloon structure (5). In at least one embodiment, at least one of one or more fluid lumens are positioned directly against or immediately adjacent to one or more balloon portions including but not limited to: a lip, a folded segment, a pleat, a radial end, a luminal end, a side length, a inner side of a side length, an outer side of a side length, an upper end of a side of a side length, a lower end of a side length, or any combination thereof to facilitate its displacement prior to the displacement by inflation fluid of another second portion of the side balloon structure (5). Sequential displacement can be accomplished by the sequential flow of fluid through a number of specifically positioned lumens against specific side balloon structure portions. Such coordinated inflation can cause Or cooperatively facilitate rotationally directed movement and momentum within the inflating side balloon structure (5).

In some embodiments the stent, its delivery system, or other portion of an assembly may include one or more areas, bands, coatings, members, etc. that are detectable by imaging modalities such as X-Ray, MRI, ultrasound, etc. In some embodiments at least a portion of the stent and/or adjacent assembly is at least partially radiopaque.

In some embodiments at least a portion of the stent is configured to include one or more mechanisms for the delivery of a therapeutic agent. Often the agent will be in the form of a coating or other layer (or layers) of material placed on a surface region of the stent, which is adapted to be released at the site of the stent's implantation or areas adjacent thereto.

The therapeutic agent can be at least one or various types of therapeutic agents including but not limited to: at least one restenosis inhibiting agent that comprises drug, polymer and bio-engineered materials or any combination thereof. In addition, the coating can be a therapeutic agent such as at least one drug, or at least one other pharmaceutical product such as non-genetic agents, genetic agents, cellular material, etc. Some examples of suitable non-genetic therapeutic agents include but are not limited to: at least one anti-thrombogenic agents such as heparin, hepatin derivatives, vasculai cell growth promoters, growth factor inhibitors, Paclitaxel, etc. Where an agent includes a genetic therapeutic agent, such a genetic agent may include but is not limited to: DNA, RNA and their respective derivatives and/or components; hedgehog proteins, etc. Where a therapeutic agent includes cellular material, the cellular material may include but is not limited to: cells of human origin and/or non-human origin as well as their respective components and/or derivatives thereof. Where the therapeutic agent includes a polymer agent, the polymer agent may be a polystyrene-polyisobutylene-polystyrene triblock copolymer (SIBS), polyethylene oxide, silicone rubber and/or any other suitable substrate. It will be appreciated that other types of coating substances, well known to those skilled in the art, can be applied to the stent (1) as well.

This completes the description of the preferred and alternate embodiments of the invention. The above disclosure is intended to be illustrative and not exhaustive. This description will suggest many variations and alternatives to one of ordinary skill in this art. The various elements shown in the individual figures and described above may be combined, substituted, or modified for combination as desired. All these alternatives and variations are intended to be included within the scope of the claims where the term "comprising" means "including, but not limited to".

Further, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all prior claims which possess all antecedents referenced in such dependent claim if such multiple dependent format is an accepted format within the jurisdiction (e.g. each claim depending directly from claim 1 should be alternatively taken as depending from all previous claims). In jurisdictions where multiple dependent claim formats are restricted, the following dependent claims should each be also taken as alternatively written in each singly dependent claim format which creates a dependency from a prior antecedent-possessing claim other than the specific claim listed in such dependent claims below.

The invention claimed is:

1. A balloon catheter comprising a balloon inflation system, the balloon inflation system comprising a side branch balloon structure, capable of at least partially expanding a side branch structure of a bifurcated stent, wherein:
the side branch balloon structure has an inflated configuration having a radial end, a luminal end and a side wall there between, where the radial end is distal from the luminal end and the luminal end is abutting the balloon catheter and;
an un-inflated configuration and when in the un-inflated configuration the side branch balloon structure is in-folded in a pleated or overlapping fold pattern from a cup fold where the radial end is flush with the luminal end and the side wall extends entirely around a cavity having an open end opposite the radial end, wherein the pleated or overlapping fold pattern permits orderly unfolding when the side branch is inflated;
wherein the side branch balloon structure is in the un-inflated configuration.

2. The balloon catheter of claim 1 further comprising a main branch balloon structure capable of inflating a main tubular body of said bifurcated stent wherein:
the side branch balloon structure and the main branch balloon structure are in fluid communication with each other.

3. The balloon catheter of claim 1 further comprising a main branch balloon structure capable of inflating a main tubular body of said bifurcated stent wherein:
the side branch balloon structure and the main branch balloon structure are not in fluid communication with each other.

4. The balloon catheter of claim 1 further comprising a main branch central axis and wherein:
when the side branch balloon structure is in the inflated configuration the radial end being further away from the main branch central axis than the luminal end, and
while the side branch balloon structure remains in the un-inflated configuration the radial and luminal ends are substantially adjacent to each other.

5. The balloon catheter of claim 4 wherein in the un-inflated configuration, the side branch balloon structure is folded such that at least some of the side wall lies flush against and over the radial end.

6. The balloon catheter of claim 5 wherein at least some of the side wall is in-folded into pleats.

7. The balloon catheter of claim 6 wherein at least some of the pleats are of different sizes.

8. The balloon catheter of claim 5 wherein at least some of the side wall is in-folded into overlapping folds.

9. The balloon catheter of claim 8 wherein at least some of the overlapping folds are of different sizes.

10. The balloon catheter of claim 5 wherein the side wall is folded into three or more segments with overlapping regions between the folded segments, at least one segment lies above one overlapping region and beneath one overlapping region.

11. The balloon catheter of claim 10 wherein every folded segment lies above one overlapping region and beneath one overlapping region.

12. The balloon catheter of claim 1 wherein the pattern is generally uniform about a side branch axis.

13. The balloon catheter of claim 1 further comprising a stent and a catheter shaft, the stent comprises a main tubular body and a side branch assembly having an iris and a crown configuration,
the stent is disposed about the catheter shaft,
when in the crown configuration at least a portion of the side branch assembly defines a fluid lumen in fluid communication with main tubular body and extends away from the main tubular body at an oblique angle,
when in the iris configuration at least a portion of the side branch assembly is positioned adjacent to the orderly folded side branch balloon structure.

14. The balloon catheter of claim 13 in which the side branch assembly comprises one or more petals which when crowned define at least a portion of the second fluid lumen, the orderly folded pattern having smooth portions of the side branch balloon structure lying against the petals.

15. The balloon catheter of claim 14 in which the smooth portions of the side branch balloon structure lie flush against the petals.

16. The balloon catheter of claim 1 in which the folded pattern allows for at least a portion of the side branch balloon structure to inflate in a sweeping rotational motion.

17. A balloon catheter comprising a balloon inflation system, the balloon inflation system comprising a side branch balloon structure, capable of at least partially expanding a side branch structure of a bifurcated stent, wherein:
the side branch balloon structure has an inflated configuration having a radial end, a luminal end and a side wall there between, where the radial end is distal from the luminal end and the luminal end is abutting the balloon catheter and;
an un-inflated configuration and when in the un-inflated configuration the side branch balloon structure is in-folded in a pleated or overlapping fold pattern from a cup fold where the radial end is flush with the luminal end, wherein the pleated or overlapping fold pattern permits orderly unfolding in which the folded pattern allows for at least a portion of the side branch balloon structure to inflate by first primarily expanding in a circumferential direction away from a center of the side branch balloon structure and later primarily expanding in a radial direction when the side branch is inflated; wherein the side branch balloon structure is in the un-inflated configuration.

* * * * *